(12) United States Patent
Acres et al.

(10) Patent No.: US 9,207,231 B2
(45) Date of Patent: Dec. 8, 2015

(54) BIOMARKER FOR SELECTING PATIENTS AND RELATED METHODS

(71) Applicant: Transgene SA, Illkirch Graffenstaden (FR)

(72) Inventors: Bruce Acres, Strasbourg (FR); Bérangère Marie-Bastien, Matzenheim (FR)

(73) Assignee: Transgene SA, Illkirch Graffenstaden Cedex (FR)

( * ) Notice: Subject to any disclaimer, the term of this patent is extended or adjusted under 35 U.S.C. 154(b) by 6 days.

(21) Appl. No.: 14/030,780

(22) Filed: Sep. 18, 2013

(65) Prior Publication Data

US 2014/0086958 A1 Mar. 27, 2014

Related U.S. Application Data

(62) Division of application No. 12/811,364, filed as application No. PCT/EP2009/003783 on May 27, 2009, now abandoned.

(60) Provisional application No. 61/108,145, filed on Oct. 24, 2008, provisional application No. 61/141,093, filed on Dec. 29, 2008.

(30) Foreign Application Priority Data

| May 29, 2008 | (EP) | 08305212 |
| Dec. 2, 2008 | (EP) | 08305876 |
| Apr. 7, 2009 | (EP) | 09305293 |

(51) Int. Cl.
| A61K 35/12 | (2015.01) |
| A61K 39/00 | (2006.01) |
| A61K 38/00 | (2006.01) |
| G01N 33/50 | (2006.01) |

(52) U.S. Cl.
CPC .......... *G01N 33/505* (2013.01); *A61K 39/0011* (2013.01); *A61K 2039/5256* (2013.01); *A61K 2039/55522* (2013.01); *C12N 2710/24143* (2013.01)

(58) Field of Classification Search
None
See application file for complete search history.

(56) References Cited

U.S. PATENT DOCUMENTS

2002/0081635 A1  6/2002  Thomas et al.

OTHER PUBLICATIONS

J. M. Schapiro et al., "Natural Killer (NK) Cell Response After Vaccination of Volunteers With Killed Influenza Vaccine," Journal Medical Virology, 30:196-200 (1990).
International Search Report and Written Opinion mailed Oct. 12, 2009, for Application No. PCT/EP2009/003783, filed May 27, 2009.
T.K. Berthoud et al., "Comparing human T cell and NK cell responses in viral-based malaria vaccine trials," Vaccine, 28: 21-27 (2010).
S.E. Chisholm et al., "Recognition of Vaccinia Virus-Infected Cells by Human Natural Killer Cells Depends on Natural Cytotoxicity Receptors," J. Virology, 80(5): 2225-2233 (2006).
J.C. Kelly, "Lung Cancer Vaccine Improves Progression-Free Survival," from http://www.medscape.com/viewarticle/752290, Abstract from Lancet Oncol., published online Oct. 22, 2011 (2 pages).
J. Kutza et al, "Natural Killer Cell Cytotoxicity in Elderly Humans after Influenza Immunization," Clin. Diag. Lab. Immunol., 3(1): 105-108 (1996).
P.A. Lang et al., "Natural killer cell activation enhances immune pathology and promotes chronic infection by limiting CD8+ T-cell immunity," Proc. Natl. Acad. Sci, USA, 109(4): 1210-1215 (2012).
E. Narni-Mancinelli et al., "Tuning of Natural Killer Cell Reactivity by NKp46 and Helios Calibrates T Cell Responses," Science, 335: 344-348 (2012).
E. Narni-Mancinelli et al., "Supporting Online Material for 'Tuning of Natural Killer Cell Reactivity by NKp46 and Helios Calibrates T Cell Responses,'" www.sciencemag.org/cgi/content/full/335/6066/344/DC1, 27 pages (2012).
A.K. Parker et al., "Induction of Natural Killer Cell Responses by Ectromelia Virus Controls Infection," J. Virol., 81(8): 4070-4079 (2007).
E. Quoix et al., "Therapeutic vaccination with TG4010 and first-line chemotherapy in advanced non-small-cell lung cancer: a controlled phase 2B trial," Lancet Oncol., 12(12):1125-1133 (2011).
M.C. Ruzek et al., "Adenoviral Vectors Stimulate Murine Natural Killer Cell Responses and Demonstrate Antitumor Activities in the Absence of Transgene Expression," Mol. Therap., 5(2): 115-124 (2002).
E. Vivier et al., "Functions of natural killer cells," Nature Immunol., 9(5): 503-510 (2008).
S. Worku et al., "Canarypox Vaccines Induce Antigen-Specific Human γδ T Cells Capable of Interferon-γ Production," J. Infectious Diseases, 184: 525-532 (2001).
First Office Action, mailed Aug. 23, 2012, for Chinese Patent Application No. 200980119675.5 (6 pages), with English translation (2 pages).
E.M. Levy et al., "Natural Killer Cells in Human Cancer: From Biological Functions to Clinical Applications," Journal of Biomedicine and Biotechnology, vol. 2011, Article ID 676198, 11 pages, doi:10.1155/2011/676198.
E. Vivier et al., "Targeting Natural Killer Cells and Natural Killer T Cells in Cancer," Nature Reviews Immunology, 12:239-244, Apr. 2012.

(Continued)

*Primary Examiner* — Michail Belyavskyi
(74) *Attorney, Agent, or Firm* — Finnegan, Henderson, Farabow, Garrett & Dunner, L.L.P.

(57) ABSTRACT

The present invention concerns methods for inducing an immune response to an antigen in a patient for treating human disease by administering an immunogenic composition wherein said patient is selected in a patient population of interest. The present invention further concerns methods for determining whether a subject is or is not susceptible to developing a prophylactic or therapeutic immune response after such treatment.

21 Claims, 4 Drawing Sheets

(56) References Cited

OTHER PUBLICATIONS

Figure 1:
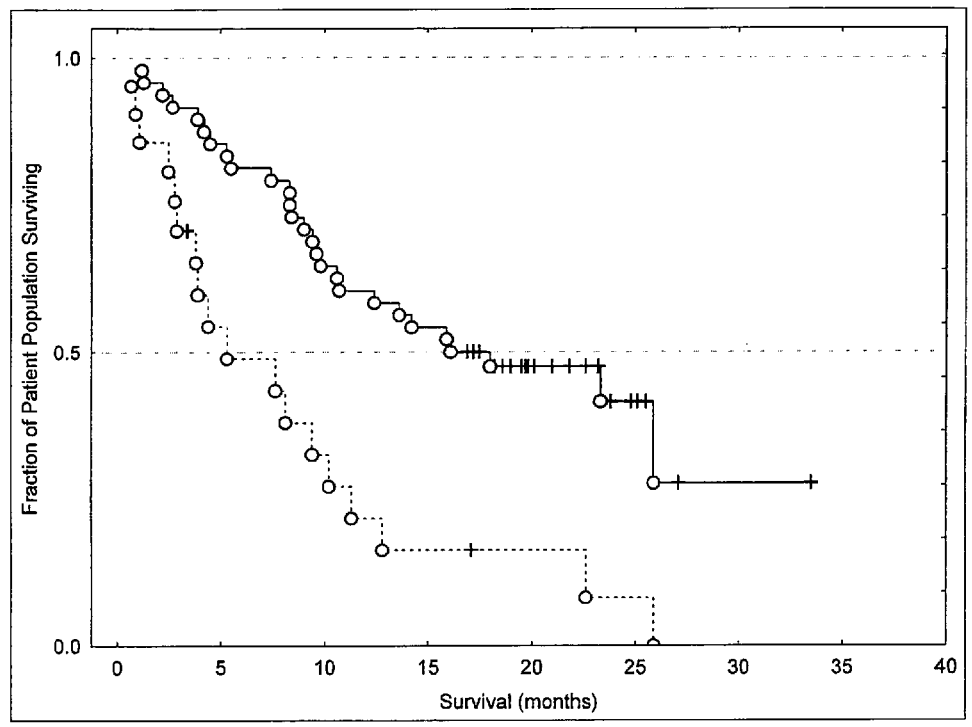

E. Vivier et al., "Innate or Adaptive Immunity? The Example of Natural Killer Cells", Science, 331(6013): 44-49, Jan. 7, 2011 (NIH Public Access Author Manuscript version; 14 pages).

Office Action, mailed Dec. 20, 2012, for Taiwan Patent Application No. 098117813 (4 pages), with English translation (2 pages).

Y. Kamoda et al., "Role of Activated Natural Killer Cells in Oral Diseases," Jpn. J. Infect. Dis., 61: 469-474 (2008).

Second Office Action, mailed Apr. 26, 2013, for Chinese Patent Application No. 200980119675.5 (4 pages), with English translation (2 pages).

BIOMARKER FOR SELECTING PATIENTS AND RELATED METHODS

CROSS REFERENCE TO RELATED APPLICATIONS

This application is a division of U.S. patent application Ser. No. 12/811,364, with 35 USC §371(c) date Jul. 2, 2010, now abandoned, which is the U.S. National Stage filing of International Application No. PCT/EP2009/003783, filed May 27, 2009, which claims priority to European Patent Application Nos. 08 305 212.6, filed May 29, 2008; 08 305 876.8, filed Dec. 2, 2008; and 09 305 293.4, filed Apr. 7, 2009, and claims priority to U.S. Provisional Application Nos. 61/108,145, filed Oct. 24, 2008; and 61/141,093, filed Dec. 29, 2008. All of the above-listed applications are incorporated by reference herein.

The present invention relates to the field of immunology and, in particular, to immunotherapy of a patient against diseases caused for example by infection or cancers. More particularly, the invention relates to methods for predicting whether a patient is or is not susceptible to developing a prophylactic or therapeutic immune response after such immunotherapy. The present invention relates to methods and compositions for improving the survival rate of patients to be treated by an immunogenic composition, in particular a vaccine.

Traditional vaccination techniques involving the introduction into an animal system of an antigen (e.g. peptides, proteins) which can induce an immune response, and thereby protect said animal against infection for example, have been known for many years. These techniques have further included the development of both live and inactivated vaccines. Live vaccines are typically attenuated non-pathogenic versions of an infectious agent that are capable of priming an immune response directed against a pathogenic version of the infectious agent.

Numerous research groups have also investigated the use of vaccines as a potential therapeutic modality for various cancer types. This specific type of vaccine strategy is generally referred to as immunotherapy.

In recent years there have been advances in the development of recombinant vaccines, especially recombinant live vaccines, in which foreign antigens of interest are encoded and expressed from a vector. Among them, vectors based on recombinant viruses have shown great promise and play an important role in the development of new vaccines. Many viruses have been investigated for their ability to express proteins from foreign pathogens or tumoral tissue, and to induce specific immunological responses against these antigens in vivo. Generally, these gene-based vaccines can stimulate potent humoral and cellular immune responses and viral vectors may be an effective strategy for both the delivery of antigen-encoding genes and the facilitation and enhancement of antigen presentation. In order to be utilized as a vaccine carrier, the ideal viral vector should be safe and enable efficient presentation of required pathogen-specific antigens to the immune system. Furthermore, the vector system must meet criteria that enable its production on a large-scale basis. Several viral vaccine vectors have thus emerged to date, all of them having relative advantages and limits depending on the proposed application (for a review on recombinant viral vaccines see for example Harrop and Carroll, 2006, Front Biosci., 11, 804-817; Yokoyama et al., 1997, J Vet Med Sci., 59, 311-322).

Following the observation in the early 1990's that plasmid DNA vectors could directly transfect animal cells in vivo, significant research efforts have also been undertaken to develop vaccination techniques based upon the use of DNA plasmids to induce immune response, by direct introduction into animals of DNA which encodes for antigens. Such techniques which are widely referred as DNA vaccination have now been used to elicit protective immune responses in large number of disease models. For a review on DNA vaccines, see Reyes-Sandoval and Ertl, 2001 (Current Molecular Medicine, 1, 217-243).

A general problem in vaccine field however has been the identification of a means of inducing a sufficiently strong immune response in vaccinated individuals to protect and/or treat against infection and disease, and thereby to extend the survival of patient having fatal disease, for example, cancer.

Therefore there has been for example major effort in recent years, to discover new drug compounds that act by stimulating certain key aspects of the immune system which will serve to increase the immune response induced by vaccines. Most of these compounds, referred as immune response modifiers (IRMs) or adjuvants, appear to act through basic immune system mechanisms via Toll-like receptors (TLRs) to induce various important cytokines biosynthesis (e.g., interferons, interleukins, tumor necrosis factor, etc. see for example Schiller et al., 2006, Exp Dermatol., 15, 331-341). Such compounds have been shown to stimulate a rapid release of certain dendritic cell, monocyte/macrophage-derived cytokines and are also capable of stimulating B cells to secrete antibodies which play an important role in the antiviral and antitumor activities of IRM compounds.

Alternatively, vaccination strategies have been proposed, most of them being based on a prime-boost vaccination regimen. According to these "prime-boost" vaccination protocols, the immune system is first induced by administering to the patient a priming composition and then boosted by administration of a boosting second composition (see for example EP1411974 or US20030191076).

It has been shown that functional activation and downregulation of natural killer (NK) cell cytotoxicity may play a major role in reproductive outcome (Nitrivalas et al., 2001, Human Reproduction, 16, 855-861). More specifically, Thum et al, 2004, Human Reproduction, 19, 2395-2400, have evaluated the effect of the absolute count of specific marker expression on peripheral blood natural killer (NK) cells on implantation and miscarriage rates after Intra Vitro Fecondation (IVF) treatment. The authors have determined that an increase in the absolute count of activated NK cells in the peripheral blood is associated with a reduced rate of embryo implantation in IVF treatment. Furthermore, women with high peripheral blood NK cell absolute count, who are able to achieve pregnancy, have a significant higher miscarriage rate.

The Applicant has now identified new tool and vaccination strategy. According to a first embodiment, the present Invention relates to a method for treating a patient for human disease by administering an immunogenic composition comprising at least one antigen wherein said patient is selected in a patient population composed of patients that have low levels of activated NK cells.

The present Invention thus relates to a method for treating a patient for human disease by administering an immunogenic composition comprising at least one antigen, said method comprising the following steps:

selection of one patient in a patient population composed of patients that have low levels of activated NK cells, administering to said selected patient the said immunogenic composition.

According to another embodiment, the present Invention relates to a method for inducing an immune response (i.e. the raised immune response) in a patient for treating human disease by administering an immunogenic composition wherein said patient is selected in a patient population composed of patients that have low levels of activated NK cells.

According to another embodiment, the present Invention relates to a method for inducing an immune response to at least one antigen (i.e. the raised immune response) in a patient for treating human disease by administering an immunogenic composition wherein said patient is selected in a patient population composed of patients that have low levels of activated NK cells.

According to another embodiment, the present Invention relates to a method for inducing an immune response (i.e. the raised immune response) in a patient for treating human disease by administering an immunogenic composition wherein said patient is selected in a patient population composed of patients that have low levels of activated NK cells and wherein said raised immune response is innate immune response. The innate immune response is body's initial immune defense against pathogens and is elicited by a variety of cells including antigen-presenting cells or "APCs". These cells express surface and cytoplasmic receptors that recognize molecules of foreign origin (e.g., bacterial and viral nucleic acids, proteins, carbohydrates). Upon detecting these signals, the dendritic cells and macrophage elicit a defensive response that includes the release of cytokines (including interferons, TNF-.alpha., and IL-12) and chemokines that attract cells such as immature dendritic cells, macrophage, NK cells, and granulocytes, to the site of challenge. The innate immune response thus confers non-specific protection while the body is generating the adaptive response.

The present Invention thus relates to a method for inducing an immune response (i.e. the raised immune response) in a patient for treating human disease by administering an immunogenic composition, said method comprising the following steps:
  selection of one patient in a patient population composed of patients that have low levels of activated NK cells,
  administering to said selected patient the said immunogenic composition.

According to another embodiment, the present Invention relates to a method for inducing an immune response to at least one antigen (i.e. the raised immune response) in a patient for treating human disease by administering an immunogenic composition, said method comprising the following steps:
  selection of one patient in a patient population composed of patients that have low levels of activated NK cells,
  administering to said selected patient the said immunogenic composition.

According to another embodiment, the present Invention relates to a method for inducing an immune response (i.e. the raised immune response) in a patient for treating human disease by administering an immunogenic composition wherein said raised immune response is innate immune response, said method comprising the following steps:
  selection of patient in a patient population composed of patients that have low levels of activated NK cells,
  administering to said selected patients the said immunogenic composition.

According to another embodiment, the present Invention relates to a method for inducing an immune response (i.e. the raised immune response) in a patient for treating human disease by administering an immunogenic composition, said method comprising the following steps:
  measuring in the patient the levels of activated NK cells, and
  administering to the patient the said immunogenic composition if said patient has low levels of activated NK cells.

According to another embodiment, the present Invention relates to a method for inducing an immune response to at least one antigen (i.e. the raised immune response) in a patient for treating human disease by administering an immunogenic composition, said method comprising the following steps:
  measuring in the patient the levels of activated NK cells, and
  administering to the patient the said immunogenic composition if said patient has low levels of activated NK cells.

According to another embodiment, the present Invention relates to a method for inducing an immune response (i.e. the raised immune response) in a patient for treating human disease by administering an immunogenic composition wherein said raised immune response is innate immune response, said method comprising the following steps:
  measuring in the patient the levels of activated NK cells, and
  administering to the patient the said immunogenic composition if said patient has low levels of activated NK cells.

According to another embodiment, the present Invention relates to a method for predicting whether a patient is or is not susceptible to developing prophylactic or therapeutic immune response by administration of an immunogenic composition, said method comprising the steps of:
  obtaining a blood sample from the patient; and
  measuring levels of activated NK cells, wherein low levels of activated NK cells indicates that the patient is predicted to have an increased susceptibility to develop a prophylactic or therapeutic immune response.

According to another embodiment, the present Invention relates to a method for selecting a patient susceptible to developing prophylactic or therapeutic immune response by administration of an immunogenic composition, said method comprising the steps of:
  obtaining a blood sample from the patient; and
  measuring levels of activated NK cells, wherein low levels of activated NK cells indicates that the patient has an increased susceptibility to developing a prophylactic or therapeutic immune response.

According to another embodiment, the present Invention relates to a method for predicting whether a patient is or is not susceptible to respond positively to a treatment comprising administration of an immunogenic composition, said method comprising the steps of:
  obtaining a blood sample from the patient; and
  measuring levels of activated NK cells, wherein low levels of activated NK cells indicates that the patient is predicted to have an increased susceptibility to develop a prophylactic or therapeutic immune response.

According to another embodiment, the present Invention relates to a method for selecting a patient susceptible to respond positively to a treatment comprising administration of an immunogenic composition, said method comprising the steps of:
  obtaining a blood sample from the patient; and
  measuring levels of activated NK cells, wherein low levels of activated NK cells indicates that the patient has an increased susceptibility to developing a prophylactic or therapeutic immune response.

According to another embodiment, the present Invention relates to an ex-vivo method for testing whether a patient will respond therapeutically to a method of treatment comprising administration of an immunogenic composition, wherein the testing method comprises the steps of:

obtaining a blood sample from the patient; and measuring levels of activated NK cells, wherein low levels of activated NK cells indicates that the patient will develop a prophylactic or therapeutic immune response towards the immunogenic composition.

According to another embodiment, the present Invention relates to an ex-vivo method for testing whether a patient will respond therapeutically to a method of treating cancer by administration of an immunogenic composition, wherein the testing method comprises the steps of:

obtaining a blood sample from the patient; and measuring levels of activated NK cells, wherein low levels of activated NK cells indicates that the patient will respond therapeutically to the method of treating cancer.

As used herein throughout the entire application, the terms "a" and "an" are used in the sense that they mean "at least one", "at least a first", "one or more" or "a plurality" of the referenced compounds or steps, unless the context dictates otherwise. For example, the term "a cell" includes a plurality of cells including a mixture thereof. More specifically, "at least one" and "one or more" means a number which is one or greater than one, with a special preference for one, two or three.

The term "and/or" wherever used herein includes the meaning of "and", "or" and "all or any other combination of the elements connected by said term".

The term "about" or "approximately" as used herein means within 20%, preferably within 10%, and more preferably within 5%.

The terms "patient", "subject" refer to a vertebrate, particularly a member of the mammalian species and includes, but is not limited to, domestic animals, sport animals, primates including humans.

As used herein, the term "treatment" or "treating" encompasses prophylaxis and/or therapy. Accordingly the immunogenic compositions or methods of the present invention are not limited to therapeutic applications and can be used in prophylaxis ones. This is covered by the term "to developing a prophylactic or therapeutic immune response" herein. "Prophylaxis" is not limited to preventing immediate diseases (e.g. infectious diseases), it further encompasses prevention of long term consequences of these infections such as cirrhosis or cancer.

An "effective amount" or a "sufficient amount" of an active compound is an amount sufficient to effect beneficial or desired results, including clinical results. An effective amount can be administered in one or more administrations. A "therapeutically effective amount" is an amount to effect beneficial clinical results, including, but not limited to, alleviation of one or more symptoms associated with viral infection as well as prevention of disease (e.g. prevention of one or more symptoms of infection).

The terms "a patient selected in a patient population composed of patients that have low levels of activated NK cells" should be understood as meaning a patient for who level of activated NK cells has been measured as disclosed herein, and who has low levels of activated NK cells. When the number of patient tested is above 1, the said patients form a patient population.

As used herein, the terms "activated NK cells" means a lymphocyte cell which expresses CD16, CD56 and CD69 cell surface antigens. According to a preferred embodiment, the said activated NK cells further does not express CD3 surface antigen. For a review, please refer to Vivier et al., 2008, Nature Immunology, 9, 503-510. Alternatively, the activated NK cells can further be defined based on expression and/or production of IL27 (Villarino et al, 2005, J Immunol., 174, 7684-91), Ly108 (Zhong and Veilette, 2008, JBC, 283(28), 19255-64), Perforin (Morissette et al., 2007, Respir Res., 8, 62), Granzyme B (Ida et al, 2003, Eur J Immunol., 33, 3284-92), IL21/21R (Frederiksen et al, 2008, Cancer Immunol Immunother., 57, 1439-49; Dodds et al., 2008, Cancer Immunol Immunother., October), CXCR1 (Inngjerdingen et al., 2001, Blood., 97, 367-75), CD244 (Gao et al., J Immunol. 2006 Mar. 1; 176(5):2758-64), IL15R and/or Granulisin. Those terms are widely used in the art.

According to special embodiments, the terms "a patient will respond therapeutically" mean that the said patient has an increase of survival rate (see example section).

According to the Invention, the levels of activated NK cells can be determined for example by flow cytometry (e.g. by flow cytofluorimetry), target cell lysis assay, and more particularly by 3 or more color flow cytometry (e.g. Beckton Dickinson, Beckman Coulter). See for example Ntrivalas et al, 2001, Human Reproduction, 16, 855-861; Borrego et al, 1993, Eur. J. Immunol., 23, 1039-1043.

According to the Invention, the levels of activated NK cells can be determined on total blood sample or on isolated peripheral blood mononuclear cells (PBMC) [e.g. by Ficoll-Hypaque purification of peripheral blood mononuclear cells (PBMC) (Bennett & Breit 1994, J Leukoc Biol., 56(3), 236-40), or by using Sigma Accuspin™ system (Sigma-Aldrich Ltd.) according to the manufacturer's instructions, and the like].

According to one embodiment of the Invention, the level of activated NK cells is determined by using antibodies.

According to one specific embodiment of the Invention, said antibodies are monoclonal antibodies.

According to one specific embodiment of the Invention, said antibodies are tagged for example by fluorescence, radiolabel, enzyme, biotin, or any other methods designed to render cells labeled with said antibodies detectable. These techniques are widely used and known in the art.

According to one preferred embodiment of the Invention, the levels of activated NK cells is determined by using antibodies specific for CD16, CD56 and/or CD69, preferably by antibodies specific for CD16, CD56 and CD69. Alternatively, said levels of activated NK cells are further determined by using antibodies specific for CD3.

Thus, for example, the levels of activated NK cells is determined by collecting peripheral blood and incubating cells with monoclonal antibodies (e.g. with anti-CD3, anti-CD4, anti-CD8, anti-CD19, anti-CD56, anti-CD69 and/or anti-CD16). Then the levels of activated NK cells is determined with the instrument, manufactured by Instrumentation Laboratory-Beckman Coulter, with a He—Ne laser-ray, which recognizes wavelengths of four different fluorochromes (fluorescein isothiocyanate FITC, phycoerythrin PE/RD1, ECD, PC5/PE).

The levels of activated NK cells can be expressed in either (i) percent (%) of peripheral blood lymphocytes which express CD16, CD56 and CD69 cell surface antigens, or (ii) absolute numbers of activated NK cells per microliter of whole peripheral blood. According to one embodiment said peripheral blood lymphocytes have been isolated from whole blood and stored frozen until analysis.

As used herein, the terms "low levels of activated NK cells" means either (i) levels of activated NK cells of less than about 5%, advantageously less than about 4.5%, preferably less than about 4% and even more preferably less than about 3.5%, and even more particularly less than about 3.45% or (ii) fewer than about 75, preferably fewer than about 60, and more preferably fewer than about 50 activated NK cells, more particularly fewer than about 35 activated NK cells, preferably those present in the mononuclear cells population, per microliter of whole peripheral blood.

As used herein, the terms "immunogenic composition" "vaccine composition", "vaccine" or similar terms can be used interchangeably and mean an agent suitable for stimulating/inducing/increasing a patient's immune system to ameliorate a current condition or to protect against or to reduce present or future harm or infections (including viral, bacterial, parasitic infections), e.g., reduced tumour cell proliferation or survival, reduced pathogen replication or spread in a patient or a detectably reduced unwanted symptom(s) associated with a condition, extend patient survival. Said immunogenic composition can contain (i) all or part of at least one targeted antigen and/or (ii) at least one recombinant vector expressing in vivo all or part of at least one heterologous nucleotide sequence, especially an heterologous nucleotide sequence encoding all or part of at least one targeted antigen. According to an alternate embodiment, the immunogenic composition of the Invention comprises (iii) at least one immune response modifier, alone or in combination with (i) and/or (ii). Examples of such immune response modifiers (IRMs), include the CpG oligonucleotides (see U.S. Pat. No. 6,194,388; US2006094683; WO 2004039829 for example), lipopolysaccharides, polyinosic:polycytidylic acid complexes (Kadowaki, et al., 2001, J. Immunol. 166, 2291-2295), and polypeptides and proteins known to induce cytokine production from dendritic cells and/or monocyte/macrophages. Other examples of such immune response modifiers (IRMs) are small organic molecule such as imidazoquinolinamines, imidazopyridine amines, 6,7-fused cycloalkylimidazopyridine amines, imidazonaphthyridine amines, oxazoloquinoline amines, thiazoloquinoline amines and 1,2-bridged imidazoquinoline amines (see for example U.S. Pat. No. 4,689,338; U.S. Pat. No. 5,389,640; U.S. Pat. No. 6,110,929; and U.S. Pat. No. 6,331,539).

As used herein, the term "antigen" refers to any substance, including complex antigen (e.g. tumour cells, virus infected cells, etc. . . . ), that is capable of being the target of an immune response. An antigen may be the target of, for example, a cell-mediated and/or humoral immune response raised by a patient. The term "antigen" encompasses for example all or part of viral antigens, tumour-specific or tumour-related antigens, bacterial antigens, parasitic antigens, allergens and the like:

Viral antigens include for example antigens from hepatitis viruses A, B, C, D and E, HIV, herpes viruses, cytomegalovirus, varicella zoster, papilloma viruses, Epstein Barr virus, influenza viruses, para-influenza viruses, adenoviruses, coxsakie viruses, picorna viruses, rotaviruses, respiratory syncytial viruses, pox viruses, rhinoviruses, rubella virus, papovirus, mumps virus, measles virus; some non-limiting examples of known viral antigens include the following: antigens derived from HIV-1 such as tat, nef, gp120 or gp160, gp40, p24, gag, env, vif, vpr, vpu, rev or part and/or combinations thereof; antigens derived from human herpes viruses such as gH, gL gM gB gC gK gE or gD or part and/or combinations thereof or Immediate Early protein such asICP27, ICP47, ICP4, ICP36 from HSV1 or HSV2; antigens derived from cytomegalovirus, especially human cytomegalovirus such as gB or derivatives thereof; antigens derived from Epstein Barr virus such as gp350 or derivatives thereof; antigens derived from Varicella Zoster Virus such as gp1, 11, 111 and 1E63; antigens derived from a hepatitis virus such as hepatitis B, hepatitis C or hepatitis E virus antigen (e.g. env protein E1 or E2, core protein, NS2, NS3, NS4a, NS4b, NS5a, NS5b, p7, or part and/or combinations thereof of HCV); antigens derived from human papilloma viruses (for example HPV6,11,16,18, e.g. L1, L2, E1, E2, E3, E4, E5, E6, E7, or part and/or combinations thereof); antigens derived from other viral pathogens, such as Respiratory Syncytial virus (e.g. F and G proteins or derivatives thereof), parainfluenza virus, measles virus, mumps virus, flaviviruses (e.g. Yellow Fever Virus, Dengue Virus, Tick-borne encephalitis virus, Japanese Encephalitis Virus) or Influenza virus cells (e.g. HA, NP, NA, or M proteins, or part and/or combinations thereof); tumor-specific or -related antigens include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, colorectal cancer, endometrial carcinoma, salivary gland carcinoma, kidney cancer, liver cancer, vulval cancer, thyroid cancer, hepatic carcinoma and various types of head and neck cancer, renal cancer, malignant melanoma, laryngeal cancer, prostate cancer. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at low levels or at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses. Some non-limiting examples of tumor-specific or -related antigens include MART-1/Melan-A, gp100, Dipeptidyl peptidase IV (DPPIV), adenosine deaminase-binding protein (ADAbp), cyclophilin b, Colorectal associated antigen (CRC)-C017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A12, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family (e.g. MUC-1), HER2/neu, p21ras, RCAS1, alpha-fetoprotein, E-cadherin, alpha-catenin, beta-catenin and gamma-catenin, p120ctn, gp100.sup.Pme1117, PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, lmp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, and c-erbB-2;

bacterial antigens includes for example antigens from *Mycobacteria* causing TB and leprosy, pneumocci, aerobic gram negative bacilli, mycoplasma, *staphyloccocal* infections, *streptococcal* infections, *salmonellae, chlamydiae, neisseriae;* other antigens includes for example antigens from malaria, leishmaniasis, trypanosomiasis, toxoplasmosis, schistosomiasis, filariasis;

allergens refer to a substance that can induce an allergic or asthmatic response in a susceptible patient. The list of allergens is enormous and can include pollens, insect venoms, animal dander dust, fungal spores and drugs (e.g. penicillin). Examples of natural, animal and plant allergens include but are not limited to proteins specific to the following genuses: Canine (*Canis familiaris*); *Dermatophagoides* (e.g. *Dermatophagoides farinae*); *Felis* (*Felis domesticus*); *Ambrosia* (*Ambrosia artemiisfolia;* Lolium (e.g. *Lolium perenne* or *Lolium multiflorum*); *Cryptomeria* (*Cryptomeria japonica*); *Alternaria* (*Alternaria alternata*); Alder; *Alnus* (*Alnus gultinoasa*); *Betula* (*Betula verrucosa*); *Quercus* (*Quercus alba*); *Olea* (*Olea europa*); *Artemisia* (*Artemisia vulgaris*); *Plantago* (e.g. *Plantago lanceolata*); *Parietaria* (e.g. *Parietaria officinalis* or *Parietaria judaica*); *Blattella* (e.g. *Blattella germanica*); *Apis* (e.g. *Apis multiflorum*); *Cupressus* (e.g. *Cupressus sempervirens, Cupressus arizonica* and *Cupressus macrocarpa*); *Juniperus* (e.g. *Juniperus sabinoides, Juniperus virginiana, Juniperus communis* and *Juniperus ashei*); *Thuya* (e.g. *Thuya orientalis*); *Chamaecyparis* (e.g. *Chamaecyparis obtuse*); *Periplaneta* (e.g. *Periplaneta americana*); *Agropyron* (e.g. *Agropyron repens*); *Secale* (e.g. *Secale cereale*); *Triticum* (e.g. *Triticum aestivum*); *Dactylis* (e.g. *Dactylis glomerata*); *Festuca* (e.g. *Festuca elatior*); *Poa* (e.g. *Poa pratensis* or *Poa compressa*); *Avena* (e.g. *Avena sativa*); *Holcus* (e.g. *Holcus lanatus*); *Anthoxanthum* (e.g. *Anthoxanthum odoratum*); *Arrhenatherum* (e.g. *Arrhenatherum elatius*); *Agrostis* (e.g. *Agrostis alba*); *Phleum* (e.g. *Phleum pratense*); *Phalaris* (e.g. *Phalaris arundinacea*); *Paspalum* (e.g. *Paspalum notatum*); *Sorghum* (e.g. *Sorghum halepensis*); and *Bromus* (e.g. *Bromus inermis*).

According to one special embodiment, said antigen is encoded by an heterologous nucleotide sequence and is expressed in vivo by a recombinant vector.

In a particularly preferred embodiment the heterologous nucleotide sequence of the present invention, encodes one or more of all or part of the following antigens HBV-PreS1 PreS2 and Surface env proteins, core and polHIV-gp120 gp40, gp160, p24, gag, pol, env, vif, vpr, vpu, tat, rev, nef; HPV-E1, E2, E3, E4, E5, E6, E7, E8, L1, L2 (see for example WO 90/10459, WO 98/04705, WO 99/03885); HCV env protein E1 or E2, core protein, NS2, NS3, NS4a, NS4b, NS5a, NS5b, p7 (see for example WO2004111082, WO2005051420); Muc-1 (see for example U.S. Pat. No. 5,861,381; U.S. Pat. No. 6,054,438; WO98/04727; WO98/37095).

According to variants of the invention, the immunogenic composition contains at least two antigens, or an heterologous nucleotide sequence encoding at least two antigens, or at least two heterologous nucleotide sequences encoding at least two antigens, or any combination thereof.

According to another special embodiment, said heterologous nucleotide sequence of the present invention, encodes all or part of HPV antigen(s) selected in the group consisting of E6 early coding region of HPV, E7 early coding region of HPV and derivates or combination thereof.

The HPV antigen encoded by the recombinant vector according to the invention is selected in the group consisting of an HPV E6 polypeptide, an HPV E7 polypeptide or both an HPV E6 polypeptide and an HPV E7 polypeptide. The present invention encompasses the use of any HPV E6 polypeptide which binding to p53 is altered or at least significantly reduced and/or the use of any HPV E7 polypeptide which binding to Rb is altered or at least significantly reduced (Munger et al., 1989, EMBO J. 8, 4099-4105; Crook et al., 1991, Cell 67, 547-556; Heck et al., 1992, Proc. Natl. Acad. Sci. USA 89, 4442-4446; Phelps et al., 1992, J. Virol. 66, 2148-2427). A non-oncogenic HPV-16 E6 variant which is suitable for the purpose of the present invention is deleted of one or more amino acid residues located from approximately position 118 to approximately position 122 (+1 representing the first methionine residue of the native HPV-16 E6 polypeptide), with a special preference for the complete deletion of residues 118 to 122 (CPEEK). A non-oncogenic HPV-16 E7 variant which is suitable for the purpose of the present invention is deleted of one or more amino acid residues located from approximately position 21 to approximately position 26 (+1 representing the first amino acid of the native HPV-16 E7 polypeptide, with a special preference for the complete deletion of residues 21 to 26 (DLYCYE). According to a preferred embodiment, the one or more HPV-16 early polypeptide(s) in use in the invention is/are further modified so as to improve MHC class I and/or MHC class II presentation, and/or to stimulate anti-HPV immunity. HPV E6 and E7 polypeptides are nuclear proteins and it has been previously shown that membrane presentation permits to improve their therapeutic efficacy (see for example WO99/03885). Thus, it may be advisable to modify at least one of the HPV early polypeptide(s) so as to be anchored to the cell membrane. Membrane anchorage can be easily achieved by incorporating in the HPV early polypeptide a membrane-anchoring sequence and if the native polypeptide lacks it a secretory sequence (i.e. a signal peptide). Membrane-anchoring and secretory sequences are known in the art. Briefly, secretory sequences are present at the N-terminus of the membrane presented or secreted polypeptides and initiate their passage into the endoplasmic reticulum (ER). They usually comprise 15 to 35 essentially hydrophobic amino acids which are then removed by a specific ER-located 1endopeptidase to give the mature polypeptide. Membrane-anchoring sequences are usually highly hydrophobic in nature and serves to anchor the polypeptides in the cell membrane (see for example Branden and Tooze, 1991, in Introduction to Protein Structure p. 202-214, NY Garland).

The choice of the membrane-anchoring and secretory sequences which can be used in the context of the present invention is vast. They may be obtained from any membrane-anchored and/or secreted polypeptide comprising it (e.g. cellular or viral polypeptides) such as the rabies glycoprotein, of the HIV virus envelope glycoprotein or of the measles virus F protein or may be synthetic. The membrane anchoring and/or secretory sequences inserted in each of the early HPV-16 polypeptides used according to the invention may have a common or different origin. The preferred site of insertion of the secretory sequence is the N-terminus downstream of the codon for initiation of translation and that of the membrane-anchoring sequence is the C-terminus, for example immediately upstream of the stop codon.

The HPV E6 polypeptide in use in the present invention is preferably modified by insertion of the secretory and membrane-anchoring signals of the measles F protein. Optionally or in combination, the HPV E7 polypeptide in use in the present invention is preferably modified by insertion of the secretory and membrane-anchoring signals of the rabies glycoprotein.

The therapeutic efficacy of the recombinant vector can also be improved by using one or more nucleic acid encoding immunopotentiator polypeptide(s). For example, it may be advantageous to link the HPV early polypeptide(s) to a polypeptide such as calreticulin (Cheng et al., 2001, J. Clin. Invest. 108, 669-678), *Mycobacterium* tuberculosis heat shock protein 70 (HSP70) (Chen et al., 2000, Cancer Res. 60, 1035-1042), ubiquitin (Rodriguez et al., 1997, J. Virol. 71, 8497-8503) or the translocation domain of a bacterial toxin such as *Pseudomonas aeruginosa* exotoxin A (ETA(dIII)) (Hung et al., 2001 Cancer Res. 61, 3698-3703).

According to another and preferred embodiment, the recombinant vector according to the invention comprises a nucleic acid encoding one or more early polypeptide(s) as above defined, and more particularly HPV-16 and/or HPV-18 early E6 and/or E7 polypeptides.

According to another special and preferred embodiment, said heterologous nucleotide sequence of the present invention, encodes all or part of MUC 1 antigen or derivates thereof.

According to another special embodiment, said heterologous nucleotide sequence of the present invention, encodes one or more of all or part of the followings: HCV env protein E1 or E2, core protein, NS2, NS3, NS4a, NS4b, NS5a, NS5b, p7 or derivates thereof. According to another special embodiment, said heterologous nucleotide sequence of the present invention, encodes one or more fusion protein wherein the configuration is not native in the sense that at least one of the NS polypeptides appears in an order which is distinct from that of the native configuration. Thus, if the fusion protein comprises a NS3 polypeptide, a NS4A polypeptide and a NS5B polypeptide, the native configuration would be NS3-NS4A-NS5B with NS3 at the N-terminus and NS5B at the C-terminus. In contrast, a non-native configuration can be NS5B-NS3-NS4A, NS5B-NS4A-NS3, NS4A-NS3-NS5B, NS4A-NS5B-NS3 or NS3-NS5B-NS4A. In particular, the fusion protein according to the invention comprises at least one of the followings:

A NS4A polypeptide fused directly or through a linker to the N-terminus of a NS3 polypeptide;

A NS3 polypeptide fused directly or through a linker to the N-terminus of a NS5B polypeptide;

A NS4B polypeptide fused directly or through a linker to the N-terminus of a NS5B polypeptide;

A NS4A polypeptide fused directly or through a linker to the N-terminus of a NS3 polypeptide which is fused directly or through a linker to the N-terminus of a NS4B polypeptide; and/or A NS3 polypeptide fused directly or through a linker to the N-terminus of a NS4B polypeptide which is fused directly or through a linker to the N-terminus of a NS5B polypeptide.

In such specific portions of the fusion protein of the invention, each of the NS polypeptides can be independently native or modified. For example, the NS4A polypeptide included in the NS4A-NS3 portion can be native whereas the NS3 polypeptide comprises at least one of the modifications described below.

If needed, the nucleic acid molecule in use in the invention may be optimized for providing high level expression of the targeted antigen (e.g. HPV early polypeptide(s)) in a particular host cell or organism, e.g. a human host cell or organism. Typically, codon optimisation is performed by replacing one or more "native" (e.g. HPV) codon corresponding to a codon infrequently used in the mammalian host cell by one or more codon encoding the same amino acid which is more frequently used. This can be achieved by conventional mutagenesis or by chemical synthetic techniques (e.g. resulting in a synthetic nucleic acid). It is not necessary to replace all native codons corresponding to infrequently used codons since increased expression can be achieved even with partial replacement. Moreover, some deviations from strict adherence to optimised codon usage may be made to accommodate the introduction of restriction site(s).

As used herein, the term "recombinant vector" refers to viral as well as non viral vectors, including extrachromosomal (e.g. episome), multicopy and integrating vectors (i.e. for being incorporated into the host chromosomes). Particularly important in the context of the invention are vectors for use in gene therapy (i.e. which are capable of delivering the nucleic acid to a host organism) as well as expression vectors for use in various expression systems. Suitable non viral vectors include plasmids such as pREP4, pCEP4 (Invitrogene), pCI (Promega), pCDMB (Seed, 1987, Nature 329, 840), pVAX and pgWiz (Gene Therapy System Inc; Himoudi et al., 2002, J. Virol. 76, 12735-12746). Suitable viral vectors may be derived from a variety of different viruses (e.g. retrovirus, adenovirus, AAV, poxvirus, herpes virus, measle virus, foamy virus and the like). As used herein, the term "viral vector" encompasses vector DNA/RNA as well as viral particles generated thereof. Viral vectors can be replication-competent, or can be genetically disabled so as to be replication-defective or replication-impaired. The term "replication-competent" as used herein encompasses replication-selective and conditionally-replicative viral vectors which are engineered to replicate better or selectively in specific host cells (e.g. tumoral cells).

In one aspect, the recombinant vector in use in the invention is a recombinant adenoviral vector (for a review, see "Adenoviral vectors for gene therapy", 2002, Ed D. Curiel and J. Douglas, Academic Press). It can be derived from a variety of human or animal sources and any serotype can be employed from the adenovirus serotypes 1 through 51. Particularly preferred are human adenoviruses 2 (Ad2), 5 (Ad5), 6 (Ad6), 11 (Ad11), 24 (Ad24) and 35 (Ad35). Such adenovirus are available from the American Type Culture Collection (ATCC, Rockville, Md.), and have been the patient of numerous publications describing their sequence, organization and methods of producing, allowing the artisan to apply them (see for example U.S. Pat. No. 6,133,028; U.S. Pat. No. 6,110,735; WO 02/40665; WO 00/50573; EP 1016711; Vogels et al., 2003, J. Virol. 77, 8263-8271).

The adenoviral vector in use in the present invention can be replication-competent. Numerous examples of replication-competent adenoviral vectors are readily available to those skill in the art (see, for example, Hernandez-Alcoceba et al., 2000, Human Gene Ther. 11, 2009-2024; Nemunaitis et al., 2001, Gene Ther. 8, 746-759; Alemany et al., 2000, Nature Biotechnology 18, 723-727). For example, they can be engineered from a wild-type adenovirus genome by deletion in the E1A CR2 domain (see for example WO00/24408) and/or by replacement of the native E1 and/or E4 promoters with tissue, tumor or cell status-specific promoters (see for example U.S. Pat. No. 5,998,205, WO99/25860, U.S. Pat. No. 5,698,443, WO00/46355, WO00/15820 and WO01/36650).

Alternatively, the adenoviral vector in use in the invention is replication-defective (see for example WO94/28152; Lusky et al., 1998, J. Virol 72, 2022-2032). Preferred replication-defective adenoviral vectors are E1-defective (see for example U.S. Pat. No. 6,136,594 and U.S. Pat. No. 6,013, 638), with an E1 deletion extending from approximately positions 459 to 3328 or from approximately positions 459 to 3510 (by reference to the sequence of the human adenovirus type 5 disclosed in the GeneBank under the accession number M 73260 and in Chroboczek et al., 1992, Virol. 186, 280-285). The cloning capacity can further be improved by deleting additional portion(s) of the adenoviral genome (all or part of the non essential E3 region or of other essential E2, E4 regions). Insertion of a nucleic acid in any location of the adenoviral vector can be performed through homologous recombination as described in Chartier et al. (1996, J. Virol. 70, 4805-4810). For example, the nucleic acid encoding the HPV-16 E6 polypeptide can be inserted in replacement of the E1 region and the nucleic acid encoding the HPV-16 E7 polypeptide in replacement of the E3 region or vice versa.

In another and preferred aspect, the vector in use in the invention is a poxviral vector (see for example Cox et al. in "Viruses in Human Gene Therapy" Ed J. M. Hos, Carolina Academic Press). According to another preferred embodiment it is selected in the group consisting of vaccinia virus, suitable vaccinia viruses include without limitation the Copenhagen strain (Goebel et al., 1990, Virol. 179, 247-266 and 517-563; Johnson et al., 1993, Virol. 196, 381-401), the Wyeth strain and the highly attenuated attenuated virus derived thereof including MVA (for review see Mayr, A., et al., 1975, Infection 3, 6-14) and derivates thereof (such as MVA vaccinia strain 575 (ECACC V00120707—U.S. Pat. No. 6,913,752), NYVAC (see WO 92/15672—Tartaglia et al., 1992, Virology, 188, 217-232). Determination of the complete sequence of the MVA genome and comparison with the Copenhagen VV genome has allowed the precise identification of the seven deletions (I to VII) which occurred in the MVA genome (Antoine et al., 1998, Virology 244, 365-396), any of which can be used to insert the antigen-encoding nucleic acid. The vector may also be obtained from any other member of the poxviridae, in particular fowlpox (e.g. TROVAC, see Paoletti et al, 1995, Dev Biol Stand., 84, 159-163); canarypox (e.g. ALVAC, WO 95/27780, Paoletti et al, 1995, Dev Biol Stand., 84, 159-163); pigeonpox; swinepox and the like. By way of example, persons skilled in the art may refer to WO 92 15672 (incorporated by reference) which describes the production of expression vectors based on poxviruses capable of expressing such heterologous nucleotide sequence, especially nucleotide sequence encoding antigen.

The basic technique for inserting the nucleic acid and associated regulatory elements required for expression in a poxviral genome is described in numerous documents accessible to the man skilled in the art (Paul et al., 2002, Cancer gene Ther. 9, 470-477; Piccini et al., 1987, Methods of Enzymology 153, 545-563; U.S. Pat. No. 4,769,330; U.S. Pat. No. 4,772,848; U.S. Pat. No. 4,603,112; U.S. Pat. No. 5,100,587 and U.S. Pat. No. 5,179,993). Usually, one proceed through homologous recombination between overlapping sequences (i.e. desired insertion site) present both in the viral genome and a plasmid carrying the nucleic acid to insert.

The nucleic acid encoding the antigen of the Invention is preferably inserted in a nonessential locus of the poxviral genome, in order that the recombinant poxvirus remains viable and infectious. Nonessential regions are non-coding intergenic regions or any gene for which inactivation or deletion does not significantly impair viral growth, replication or infection. One may also envisage insertion in an essential viral locus provided that the defective function is supplied in trans during production of viral particles, for example by using an helper cell line carrying the complementing sequences corresponding to those deleted in the poxviral genome.

When using the Copenhagen vaccinia virus, the antigen-encoding nucleic acid is preferably inserted in the thymidine kinase gene (tk) (Hruby et al., 1983, Proc. Natl. Acad. Sci USA 80, 3411-3415; Weir et al., 1983, J. Virol. 46, 530-537). However, other insertion sites are also appropriate, e.g. in the hemagglutinin gene (Guo et al., 1989, J. Virol. 63, 4189-4198), in the K1L locus, in the u gene (Zhou et al., 1990, J. Gen. Virol. 71, 2185-2190) or at the left end of the vaccinia virus genome where a variety of spontaneous or engineered deletions have been reported in the literature (Altenburger et al., 1989, Archives Virol. 105, 15-27; Moss et al. 1981, J. Virol. 40, 387-395; Panicali et al., 1981, J. Virol. 37, 1000-1010; Perkus et al, 1989, J. Virol. 63, 3829-3836; Perkus et al, 1990, Virol. 179, 276-286; Perkus et al, 1991, Virol. 180, 406-410).

When using MVA, the antigen-encoding nucleic acid can be inserted in any one of the identified deletions I to VII as well as in the D4R locus, but insertion in deletion II or III is preferred (Meyer et al., 1991, J. Gen. Virol. 72, 1031-1038; Sutter et al., 1994, Vaccine 12, 1032-1040).

When using fowlpox virus, although insertion within the thymidine kinase gene may be considered, the antigen-encoding nucleic acid is preferably introduced in the intergenic region situated between ORFs 7 and 9 (see for example EP 314 569 and U.S. Pat. No. 5,180,675).

According to one special embodiment, said recombinant vector is a recombinant plasmid DNA or a recombinant viral vector.

According to another special embodiment, said recombinant viral vector is a recombinant adenoviral vector.

According to another special embodiment, said recombinant viral vector is a recombinant vaccinia vector.

According to another special embodiment, said recombinant vaccinia vector is a recombinant MVA vector.

Preferably, the antigen-encoding nucleic acid in use in the invention is in a form suitable for its expression in a host cell or organism, which means that the nucleic acid sequence encoding the antigen are placed under the control of one or more regulatory sequences necessary for its expression in the host cell or organism. As used herein, the term "regulatory sequence" refers to any sequence that allows, contributes or modulates the expression of a nucleic acid in a given host cell, including replication, duplication, transcription, splicing, translation, stability and/or transport of the nucleic acid or one of its derivative (i.e. mRNA) into the host cell. It will be appreciated by those skilled in the art that the choice of the regulatory sequences can depend on factors such as the host cell, the vector and the level of expression desired. The nucleic acid encoding the antigen is operatively linked to a gene expression sequence which directs the expression of the antigen nucleic acid within a eukaryotic cell. The gene expression sequence is any regulatory nucleotide sequence, such as a promoter sequence or promoter-enhancer combination, which facilitates the efficient transcription and translation of the antigen nucleic acid to which it is operatively linked. The gene expression sequence may, for example, be a mammalian or viral promoter, such as a constitutive or inducible promoter. Constitutive mammalian promoters include, but are not limited to, the promoters for the following genes: hypoxanthine phosphoribosyl transferase (HPRT), adenosine deaminase, pyruvate kinase, b-actin promoter and other constitutive promoters. Exemplary viral promoters which function constitutively in eukaryotic cells include, for example, promoters from the cytomegalovirus (CMV), simian virus (e.g., SV40), papilloma virus, adenovirus, human immuno-deficiency virus (HIV), Rous sarcoma virus, cytomegalovirus, the long terminal repeats (LTR) of Moloney leukemia virus and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art. In general, the gene expression sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined antigen nucleic acid. The gene expression sequences optionally include enhancer sequences or upstream activator sequences as desired. Preferred promoters for use in a poxviral vector (see below) include without limitation vaccinia promoters 7.5K, H5R, TK, p28, p11 and K1L, chimeric promoters between early and late poxviral promoters as well as synthetic promoters such as those described in Chakrabarti et al. (1997, Biotechniques 23, 1094-1097), Hammond et al. (1997, J. Virological Methods 66, 135-138) and Kumar and Boyle (1990, Virology 179, 151-158).

The promoter is of special importance and the present invention encompasses the use of constitutive promoters which direct expression of the nucleic acid in many types of host cells and those which direct expression only in certain host cells or in response to specific events or exogenous factors (e.g. by temperature, nutrient additive, hormone or other ligand). Suitable promoters are widely described in literature and one may cite more specifically viral promoters such as RSV, SV40, CMV and MLP promoters. Preferred promoters for use in a poxviral vector include without limitation vaccinia promoters 7.5K, H5R, TK, p28, p11 and K1L, chimeric promoters between early and late poxviral promoters as well as synthetic promoters such as those described in Chakrabarti et al. (1997, Biotechniques 23, 1094-1097), Hammond et al. (1997, J. Virological Methods 66, 135-138) and Kumar and Boyle (1990, Virology 179, 151-158).

Those skilled in the art will appreciate that the regulatory elements controlling the expression of the nucleic acid molecule of the invention may further comprise additional elements for proper initiation, regulation and/or termination of transcription (e.g. polyA transcription termination sequences), mRNA transport (e.g. nuclear localization signal sequences), processing (e.g. splicing signals), and stability (e.g. introns and non-coding 5' and 3' sequences), translation (e.g. peptide signal, propeptide, tripartite leader sequences, ribosome binding sites, Shine-Dalgamo sequences, etc.) into the host cell or organism.

Alternatively, the recombinant vector in use in the present invention can further comprise at least one nucleic acid encoding at least one cytokine. Suitable cytokines include without limitation interleukins (e.g. IL-2, IL-7, IL-15, IL-18, IL-21) and interferons (e.g. IFNγ, INFα), with a special preference for interleukin IL-2. When the recombinant vaccine of the invention comprises a cytokine-expressing nucleic acid, said nucleic acid may be carried by the recombinant vector encoding the one or more antigen(s) or by an independent recombinant vector which can be of the same or a different origin.

According to one preferred embodiment, the recombinant vector in use in the present invention is encoding all or part of the MUC1 antigen and at least one cytokines above listed, and preferably an interleukin, especially IL2. Preferably the recombinant vector in use in the present invention is an MVA encoding all or part of the MUC1 antigen and at least one cytokines above listed, and preferably an interleukin, especially IL2.

Infectious viral particles comprising the above-described recombinant viral vector can be produced by routine process. An exemplary process comprises the steps of:
  a. introducing the viral vector into a suitable cell line,
  b. culturing said cell line under suitable conditions so as to allow the production of said infectious viral particle,
  c. recovering the produced infectious viral particle from the culture of said cell line, and
  d. optionally purifying said recovered infectious viral particle.

Cells appropriate for propagating adenoviral vectors are for example 293 cells, PERC6 cells, HER96 cells, or cells as disclosed in WO 94/28152, WO 97/00326, U.S. Pat. No. 6,127,175.

Cells appropriate for propagating poxvirus vectors are avian cells, and most preferably primary chicken embryo fibroblasts (CEF) prepared from chicken embryos obtained from fertilized eggs.

The infectious viral particles may be recovered from the culture supernatant or from the cells after lysis (e.g. by chemical means, freezing/thawing, osmotic shock, mechanic shock, sonication and the like). The viral particles can be isolated by consecutive rounds of plaque purification and then purified using the techniques of the art (chromatographic methods, ultracentrifugation on caesium chloride or sucrose gradient).

If desired, the method or use for treating a patient for human disease human disease according to the Invention (i.e. by administering an immunogenic composition comprising at least one antigen) can be carried out in the selected patients in conjunction with one or more conventional therapeutic modalities (e.g. radiation, chemotherapy and/or surgery). The use of multiple therapeutic approaches provides the selected patient with a broader based intervention. In one embodiment, the method or use for treating a patient for human disease human disease according to the Invention can be preceded or followed by a surgical intervention. In another embodiment, it can be preceded or followed by radiotherapy (e.g. gamma radiation). Those skilled in the art can readily formulate appropriate radiation therapy protocols and parameters which can be used (see for example Perez and Brady, 1992, Principles and Practice of Radiation Oncology, 2nd Ed. JB Lippincott Co; using appropriate adaptations and modifications as will be readily apparent to those skilled in the field). In still another embodiment, the method or use of the invention is associated to chemotherapy with one or more drugs (e.g. drugs which are conventionally used for treating or preventing viral infections, virus-associated pathologic conditions, cancer, and the like).

The present Invention thus relates to a method for improving the treatment of a cancer patient which is undergoing chemotherapeutic treatment with a chemotherapeutic agent, said method comprising the following steps:
  selection of patient in a patient population composed of patients that have low levels of activated NK cells,
  administering to said selected patients an immunogenic composition according to the Invention and a chemotherapeutic agent.

The present Invention thus relates to a method for improving the treatment of a cancer patient which is undergoing chemotherapeutic treatment with a chemotherapeutic agent, said method comprising the following steps:

measuring in the patient the levels of activated NK cells, and administering to the patient the said immunogenic composition if said patient has low levels of activated NK cells according to the Invention.

According to one embodiment, the administration of said chemotherapeutic agent is done before administration of said immunogenic composition.

According to another embodiment, the administration of said chemotherapeutic agent is done after administration of said immunogenic composition.

According to another embodiment, the administration of said chemotherapeutic agent is done concomitantly with administration of said immunogenic composition.

According to one embodiment, said chemotherapeutic agent is cisplatin and/or Gemcitabine, or equivalent thereof.

The present Invention further concerns a method of improving cytotoxic effectiveness of cytotoxic drugs or radiotherapy which comprises co-treating a patient selected in a patient population composed of patients that have low levels of activated NK cells with an immunogenic composition according to the Invention.

In another embodiment, the method or use of the invention is carried out according to a prime boost therapeutic modality which comprises sequential administration of one or more primer composition(s) and one or more booster composition(s). Typically, the priming and the boosting compositions use different vehicles which comprise or encode at least an antigenic domain in common. The priming composition is initially administered to the host organism and the boosting composition is subsequently administered to the same host organism after a period varying from one day to twelve months. The method of the invention may comprise one to ten sequential administrations of the priming composition followed by one to ten sequential administrations of the boosting composition. Desirably, injection intervals are a matter of one week to six months. Moreover, the priming and boosting compositions can be administered at the same site or at alternative sites by the same route or by different routes of administration.

According to one special embodiment, the Invention relates to a method as above described wherein said human disease is cancer.

According to a preferred embodiment, said cancer is for example breast cancer, colon cancer, kidney cancer, rectal cancer, lung cancer, cancer of the head and neck, renal cancer, malignant melanoma, laryngeal cancer, ovarian cancer, cervical cancer, prostate cancer, non Small cell Lung Cancer, haematological cancers, gastric cancers, myeloma.

According to one special embodiment, the Invention relates to a method as above described wherein said human disease is infectious disease.

According to a preferred embodiment, said infectious disease is a viral induced disease, such as for example disease induced by HIV, HCV, HBV, HPV, and the like.

In a further embodiment there is provided the use of an immunogenic composition comprising all or part of a targeted antigen for the manufacture of a medicament for treating a patient for human disease in a particular patient population wherein the patients of said population have low levels of activated NK cells.

In a further embodiment there is provided the use of an immunogenic composition for the manufacture of a medicament for inducing an immune response (i.e. the raised immune response) in a patient for treating human disease in a particular patient population wherein the patients of said population have low levels of activated NK cells.

In another embodiment there is provided the use of an immunogenic composition for the manufacture of a medicament for inducing an immune response to at least one antigen (i.e. the raised immune response) in a patient for treating human disease in a particular patient population wherein the patients of said population have low levels of activated NK cells.

In another embodiment there is provided the use of an immunogenic composition for the manufacture of a medicament for inducing an immune response to a targeted antigen (i.e. the raised immune response) in a patient for treating human disease in a particular patient population wherein the patients of said population have low levels of activated NK cells.

In another embodiment there is provided the use of an immunogenic composition for the manufacture of a medicament for inducing an immune response (i.e. the raised immune response) in a patient for treating human disease in a particular patient population wherein the patients of said population have low levels of activated NK cells and wherein said raised immune response is innate immune response.

According to one special embodiment, said "raised immune response" in said patient population is directed towards a tumour-specific or -related antigens and/or viral antigen. According to one embodiment, said "raised immune response" in said patient population is directed towards distinct antigens. According to one special embodiment, said "raised immune response" in said patient population is directed towards all or part of MUC1 antigen. According to another special embodiment, said "raised immune response" in said patient population is T cell immune response, and preferably CD8+ (Cytotoxic T Lymphocytes) immune response. According to another special embodiment, said "raised immune response" in said patient population is a non specific immune response. According to another special embodiment, said "raised immune response" in said patient population is a stimulation of the innate immune response.

The ability to induce or stimulate an immune response upon administration in an animal or human organism can be evaluated either in vitro or in vivo using a variety of assays which are standard in the art. For a general description of techniques available to evaluate the onset and activation of an immune response, see for example Coligan et al. (1992 and 1994, Current Protocols in Immunology; ed J Wiley & Sons Inc, National Institute of Health). Measurement of cellular immunity can be performed by measurement of cytokine profiles secreted by activated effector cells including those derived from CD4+ and CD8+ T-cells (e.g. quantification of IL-10 or IFN gamma-producing cells by ELIspot), by determination of the activation status of immune effector cells (e.g. T cell proliferation assays by a classical [$^3$H] thymidine uptake), by assaying for antigen-specific T lymphocytes in a sensitized patient (e.g. peptide-specific lysis in a cytotoxicity assay) or by detection of antigen specific T cells by fluorescent MHC and/or peptide multimers (e.g. tetramers). The ability to stimulate a humoral response may be determined by antibody binding and/or competition in binding (see for example Harlow, 1989, Antibodies, Cold Spring Harbor Press). The method of the invention can also be further validated in animal models challenged with an appropriate tumor-inducing agent (e.g. MUC1-expressing TC1 cells) to determine anti-tumor activity, reflecting an induction or an enhancement of an anti-antigen immune response.

Thus the present invention further concerns a method for extending the survival of a patient treated for human disease, for example cancer, by administering an immunogenic composition, said method comprising the following steps:
  selection of patient in a patient population composed of patients that have low levels of activated NK cells,
  administering to said selected patients the said immunogenic composition.

The present invention further concerns a method for extending the survival rate of a patient treated for human disease, for example cancer, by administering an immunogenic composition, said method comprising the following steps:
  measuring in the patient the levels of activated NK cells, and
  administering to the patient the said immunogenic composition if said patient has low levels of activated NK cells.

The present invention further concerns a method for extending the survival rate of a patient treated for human disease, for example cancer, by administering an immunogenic composition and chemotherapeutic agent (see above), said method comprising the following steps:
  measuring in the patient the levels of activated NK cells, and
  administering to the patient the said immunogenic composition and chemotherapeutic agent if said patient has low levels of activated NK cells.

According to another embodiment, the present Invention relates to the use of activated NK cells as a biomarker for predicting whether a patient is or is not susceptible to developing prophylactic or therapeutic immune response by administration of an immunogenic composition.

More specifically, the present Invention relates to the use of the level of activated NK cells as a biomarker for predicting whether a patient is or is not susceptible to developing prophylactic or therapeutic immune response by administration of an immunogenic composition, wherein low levels of activated NK cells indicates that the patient is predicted to have an increased susceptibility to develop a prophylactic or therapeutic immune response.

In other words, the present Invention relates to the use of the level of activated NK cells as a biomarker for predicting whether a patient is or is not susceptible to survive longer after administration of an immunogenic composition, wherein low levels of activated NK cells indicates that the patient is predicted to have a longer survival rate compared to treated patients who have higher levels of activated NK cells.

Thus the Invention further concerns the use of the level of activated NK cells as a biomarker for predicting whether a patient which is undergoing chemotherapeutic treatment with a chemotherapeutic agent is or is not susceptible to developing prophylactic or therapeutic immune response (e.g. to survive longer) after administration of an immunogenic composition.

Thus the Invention further concerns the use of the level of activated NK cells as a biomarker for predicting whether a patient which is undergoing chemotherapeutic treatment with a chemotherapeutic agent is or is not susceptible to developing prophylactic or therapeutic immune response (e.g. to survive longer) after administration of an immunogenic composition, wherein low levels of activated NK cells indicates that the patient is predicted to have an increased susceptibility to develop a prophylactic or therapeutic immune response.

The present Invention thus relates to a method for improving the treatment of a cancer patient which is undergoing chemotherapeutic treatment with a chemotherapeutic agent, said method comprising the following steps:
  measuring in the patient the levels of activated NK cells, and
  administering to the patient the said immunogenic composition if said patient has low levels of activated NK cells according to the Invention.

The present invention further concerns a method for extending the survival of a patient treated for human disease, for example cancer, by administering an immunogenic composition, said method comprising the following steps:
  measuring in the patient the levels of activated NK cells, and
  administering to the patient the said immunogenic composition if said patient has low levels of activated NK cells.

The present invention further concerns a method for extending the survival of a patient treated for human disease, for example cancer, by administering an immunogenic composition and chemotherapeutic agent (see above), said method comprising the following steps:
  measuring in the patient the levels of activated NK cells, and
  administering to the patient the said immunogenic composition and chemotherapeutic agent if said patient has low levels of activated NK cells.

The invention also provides kits (i.e. companion test) which include parts for practicing the methods described herein and that will be apparent from the examples provided herein. The kit of parts, or kits, may include reagents for collecting and or measuring serum levels of activated NK cells. Such reagents may include antibodies. The kits may further include equipment for collecting and/or processing biological samples. The kits are also likely to contain instructions for use, cut-off values and/or instructions for their determination, and instructions for interpreting the data obtained from the use of the kits.

According to one special embodiment, the said kit of parts, or kits, may further include an immunogenic composition as above disclosed, and/or as disclosed in the Example section below.

The invention further provides computer programs and/or algorithms for monitoring clinical trial and activated NK cells levels, determining whether such levels are above or below a threshold level, and/or recommending modifications to a treatment regiment to improve a patient's response to an immunotherapy treatment. The computer programs or algorithms may be provided along with necessary hardware, e.g., in the form of a kit or apparatus, which may also accept biological samples and measure the relative levels of activated NK cells present therein. The above-described computer programs and/or apparatus are likely to be provided to physicians or clinical laboratories with appropriate instructions and reagents, including antibodies.

The invention has been described in an illustrative manner, and it is to be understood that the terminology which has been used is intended to be in the nature of words of description rather than of limitation. Obviously, many modifications and variations of the present invention are possible in light of the above teachings. It is therefore to be understood that within the scope of the appended claims, the invention may be practiced in a different way from what is specifically described herein.

All of the above cited disclosures of patents, publications and database entries are specifically incorporated herein by reference in their entirety to the same extent as if each such individual patent, publication or entry were specifically and individually indicated to be incorporated by reference.

EXAMPLES

Figures

FIG. 1: Survival curves describing vaccine immunotherapy in lung cancer: patients with < or ≥3.45% Activated NK
- Group 1: Vaccine (i.e. immunogenic composition)+chemotherapy in patients with low levels of activated NK cells. Low levels as defined as <3.45% CD16+ CD56+ CD69+ lymphocytes in peripheral blood. 48 patients
- Group 2: Vaccine+chemotherapy in patients with high levels of activated NK cells. High levels as defined as ≥3.45% CD16+ CD56+ CD69+ lymphocytes in peripheral blood. 21 patients
- Significant difference, by log rank: p=0.0018
- ○ Complete + Censored FIG. 2: Survival curves describing vaccine immunotherapy in lung cancer: patients who have < or ≥35 Activated NK per μl whole blood.
- Group 1: Vaccine+chemotherapy in patients with low levels of activated NK cells. Low levels as defined as <35 CD16+ CD56+ CD69+ lymphocytes per μl of peripheral blood. 33 patients.
- Group 2: Vaccine+chemotherapy in patients with high levels of activated NK cells. High levels as defined as ≥35 CD16+ CD56+ CD69+ lymphocytes per μl peripheral blood. 22 patients.
- Significant difference, by log rank: p=0.017
- ○ Complete + Censored FIG. 3: Survival curves describing chemotherapy in lung cancer: patients with < or ≥3.45% Activated NK
- Group 1: Chemotherapy alone (without vaccine) in patients with low levels of activated NK cells. Low levels as defined as <3.45% CD16+ CD56+ CD69+ lymphocytes in peripheral blood. 53 patients.
- Group 2: Chemotherapy alone (without vaccine) in patients with high levels of activated NK cells. High levels as defined as >3.45% CD16+ CD56+ CD69+ lymphocytes in peripheral blood. 16 patients.
- Significant difference, by log rank: p=0.30 (not statistically significant)
- ○ Complete + Censored FIG. 4: Survival curves describing chemotherapy in lung cancer: patients who have < or ≥35 Activated NK per μl whole blood.
- Group 1: Chemotherapy alone (without vaccine) in patients with low levels of activated NK cells. Low levels as defined as <35 CD16+ CD56+ CD69+ lymphocytes per μl of peripheral blood. 45 patients.
- Group 2: Chemotherapy alone (without vaccine). 16 patients
- Significant difference, by log rank: p=0.08 (not significant)
- ○ Complete + Censored

Example 1

The immunogenic composition, noted vaccine TG4010, was used to treat non-small cell lung cancer (NSCLC) patients in combination with standard chemotherapy.

TG4010 is a recombinant Modified Virus Ankara (MVA) expressing both 1L2 and the tumor-associated antigen MUC1.

One hundred and forty eight patients were randomized to receive:
- chemotherapy (Cisplatin 75 mg/m² on d1 and Gemcitabine 1250 mg/m² on day 1 and day 8 every 3 weeks for up to 6 cycles either alone (Study Arm 2) or
- chemotherapy together with TG4010 (Study Arm 1).

Tumors were evaluated (WHO criteria) every 6 weeks. Endpoints were progression-free survival (PFS) at 6 months and overall survival with intent to treat analysis.

Blood samples were taken prior to treatment and were shipped immediately to a central immunology lab where peripheral blood mononuclear cells (PBMC) were isolated from the blood and stored frozen until analysis.

PBMC were assessed for the expression of CD16, CD56 and CD69 by flow cytometry using monoclonal antibodies specific for those antigens (IM0814, IM2073 and IM2656, respectively, all from Beckman Coulter). The proportion of cells expressing these antigens can be expressed as % of total lymphocytes evaluated or numbers of CD16+ CD56+ and CD69+ in the PBMC population per μl of whole blood.

FIG. 1 shows that patients [Arm 1 (TG4010+chemotherapy)] with <3.45% CD16+ CD56+ CD69+ lymphocytes at baseline survive longer (median survival=16.1 months) than do patients with ≥3.45% CD16+ CD56+ CD69+ lymphocytes (median survival 17.1 months) when treated with both the TG4010 vaccine and chemotherapy.

Figure 2:
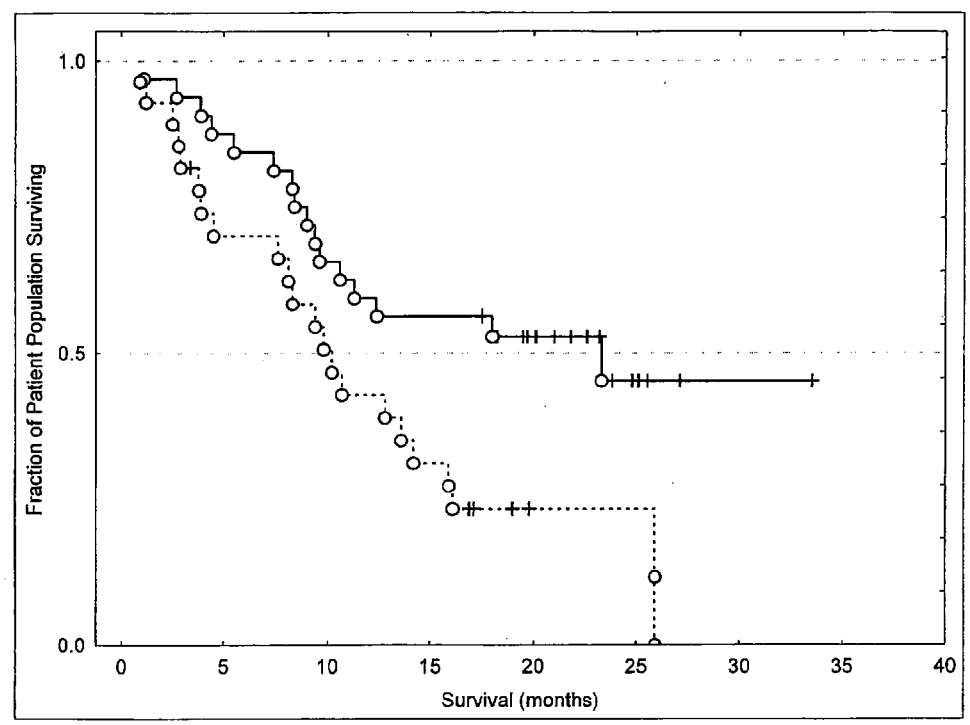

Similarly, the data in FIG. 2 show that the same results are achieved if patients are selected on the basis of < or >35 CD16+ CD56+ CD69+ lymphocytes per μl of whole blood (based on measurement using PBMC). Patients with <35 CD16+ CD56+ CD69+ lymphocytes per μl of whole blood (based on measurement of PBMC) survive longer (median survival=19.9 months) than patients with ≥35 CD16+ CD56+ CD69+ lymphocytes per μl of whole blood (based on measurement of PBMC) (median survival=9.9 months).

Figure 3:
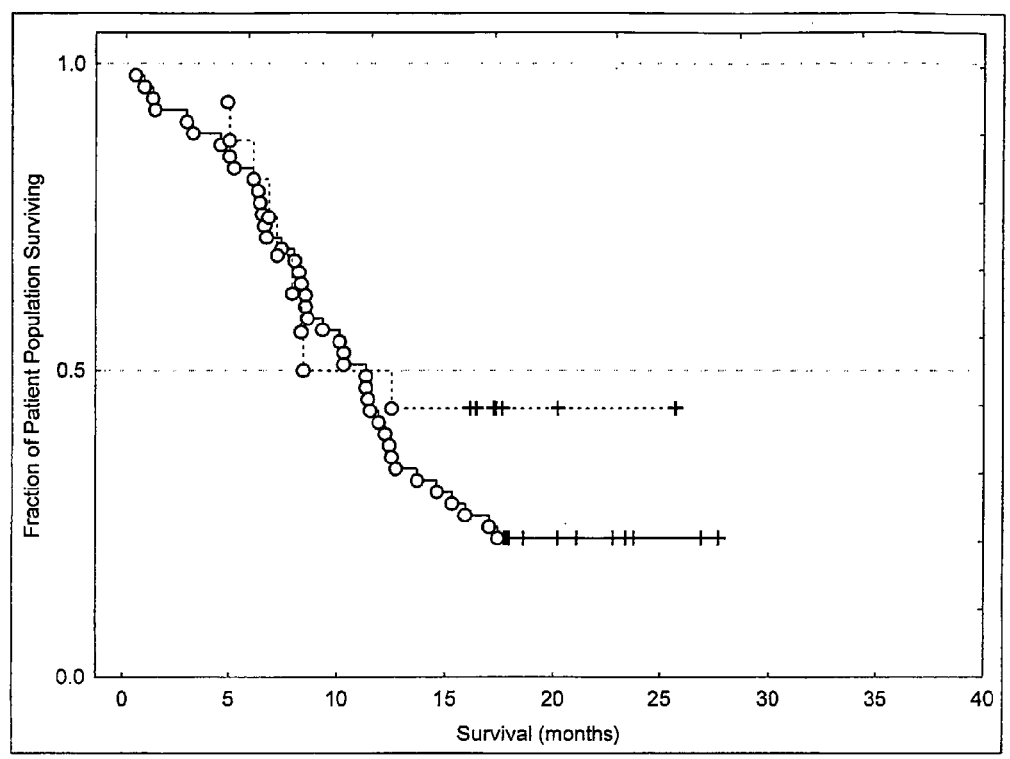
Figure 4:
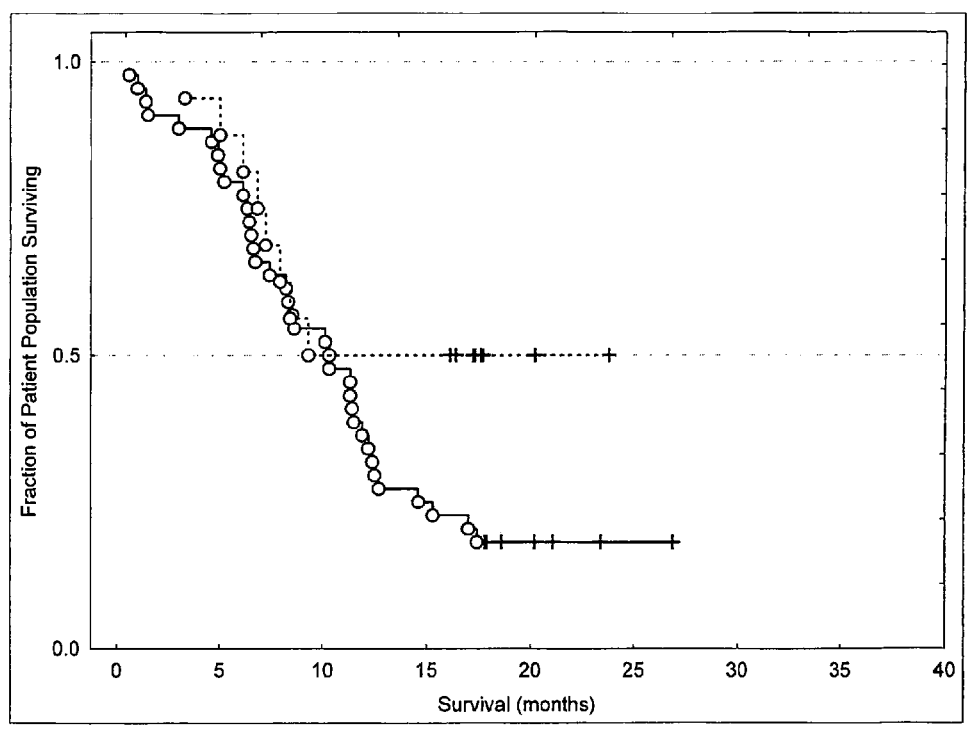

The data in FIGS. 3 and 4 demonstrate that the effect of selecting patients based on the expression of CD16, CD56 and CD69 on their lymphocytes is restricted to patients receiving the vaccine. FIG. 3 shows that patients with < or ≥3.45% CD16+ CD56+ CD69+ lymphocytes at baseline have the same survival expectancy. FIG. 4 shows that the observation using 35 CD16+ CD56+ CD69+ lymphocytes per μl whole blood at baseline.

The invention claimed is:

1. A method of inducing an immune response in a cancer patient, the method comprising: administering to a patient a composition comprising at least one recombinant viral vector expressing at least one heterologous nucleotide sequence,
    wherein the level of activated NK cells in a peripheral blood sample from the patient is less than about 5% prior to administration; and
    wherein the level of activated NK cells has been measured by determining the level of CD16, CD56 and CD69 cell surface antigens expressed by peripheral blood lymphocytes in the sample using an antibody-based assay.

2. The method of claim 1, wherein the level of activated NK cells is measured by flow cytometry.

3. The method of claim 1, wherein the level of activated NK cells is measured using antibodies specific for CD16, CD56 and CD69 cell surface antigens.

4. The method of claim 1, wherein the peripheral blood sample is whole peripheral blood or isolated peripheral blood mononuclear cells.

5. The method of claim 1, wherein the recombinant viral vector is replication-competent.

6. The method of claim 1, wherein the recombinant viral vector is replication-defective.

7. The method of claim 1, wherein the recombinant viral vector is a recombinant adenoviral vector.

8. The method of claim 1, wherein the recombinant viral vector is a recombinant vaccinia vector.

9. The method of claim 8, wherein the recombinant vaccinia vector is a recombinant MVA vector.

10. The method of claim 9, wherein the recombinant MVA vector expresses interleukin 2 (IL2) and the tumor-associated antigen MUC1.

11. The method of claim 1, wherein the patient is further treated with a chemotherapeutic agent.

12. The method of claim 1 wherein the recombinant viral vector expresses interleukin 2 (IL2) and the tumor-associated antigen MUC1.

13. The method of claim 1, wherein the patient suffers from non small-cell lung cancer (NSCLC).

14. The method of claim 13, wherein the recombinant viral vector expresses interleukin 2 (IL2) and the tumor-associated antigen MUC1.

15. The method of claim 1, wherein the level of activated NK cells is measured using antibodies specific for CD16, CD56, CD69, and CD3 cell surface antigens expressed by the peripheral blood lymphocytes in the sample.

16. A method of inducing an immune response in a cancer patient, the method comprising: administering to a patient a composition comprising at least one recombinant viral vector expressing at least one heterologous nucleotide sequence, wherein the level of activated NK cells in a peripheral blood sample from the patient is less than about 3.5% prior to administration, and
wherein the level of activated NK cells has been measured by determining the level of CD16, CD56 and CD69 cell surface antigens expressed by peripheral blood lymphocytes in the sample using an antibody-based assay.

17. The method of claim 16, wherein the recombinant viral vector expresses interleukin 2 (IL2) and the tumor-associated antigen MUC1.

18. The method of claim 17, wherein the recombinant viral vector is an MVA vector.

19. The method of claim 16, wherein the patient suffers from non small-cell lung cancer (NSCLC).

20. The method of claim 19, wherein the recombinant viral vector expresses interleukin 2 (IL2) and the tumor-associated antigen MUC1.

21. The method of claim 16, wherein said patient is further treated with a chemotherapeutic agent.

* * * * *